US00PP13866P39

(12) United States Plant Patent
Kos

(10) Patent No.: US PP13,866 P3
(45) Date of Patent: Jun. 10, 2003

(54) LILY PLANT NAMED 'ORANIA'

(75) Inventor: Pieter Jan Kos, Nieuweweg (NL)

(73) Assignee: World Breeding, B.V. (NL)

( * ) Notice: Subject to any disclaimer, the term of this patent is extended or adjusted under 35 U.S.C. 154(b) by 0 days.

(21) Appl. No.: 09/834,745

(22) Filed: Apr. 13, 2001

(65) Prior Publication Data

US 2001/0056584 P1 Dec. 27, 2001

(51) Int. Cl.[7] ..... A01H 5/00
(52) U.S. Cl. ..... Plt./313
(58) Field of Search ..... Plt./313

(56) References Cited

PUBLICATIONS

The New Royal Horticultural Society Dictionary of Gardening, vol. 3, editor–in–chief Anthony Huxley, The Royal Horticultural Society, 1992, pp. 68–80.*

* cited by examiner

*Primary Examiner*—Bruce R. Campell
*Assistant Examiner*—Anne Marie Grünberg
(74) *Attorney, Agent, or Firm*—Klarquist Sparkman LLP

(57) ABSTRACT

A new and distinct variety of upright Oriental×Aurelia hybrid lily plant, named 'Orania', characterized by large, orange flowers.

1 Drawing Sheet

LATIN NAME OF THE GENUS AND SPECIES OF THE PLANT CLAIMED

Genus: Lilium. Species is unknown.

VARIETY DENOMINATION

'Orania'.

BACKGROUND OF THE INVENTION

The present invention relates to a new and distinct variety of Lilium hybrid referred to commercially as an upright Oriental×Aurelia lily hybrid and given the varietal name 'Orania'.

This new variety is the product of a controlled breeding program using embryo culture and was carried out in the municipality of Breezand, The Netherlands, using the proprietary Oriental type hybrid lily 93.50.108-6 as the seed parent and the proprietary Aurelia type hybrid lily 87.319-1 as the pollen parent. Compared to the typical characteristics of common Oriental and Aurelia type lily hybrids, 'Orania' has larger flowers, taller plant height and taller stems, and blooms earlier.

This new variety has not been observed under all possible environmental conditions. The phenotype may vary significantly with variations in environment such as temperature, light intensity, day length, and nutrient availability, without, however, any variations in genotype.

BRIEF SUMMARY OF THE INVENTION

The following traits have been repeatedly observed and are determined to be the basic characteristics of this invention that, in combination, distinguish 'Orania' as a new and distinct lily variety:

1. floriferous habit;
2. large orange flowers;
3. vigorous growth habit;
4. tall plant;
5. good virus tolerance, and 6. excellent vase-life.

Bulbs of this plant may be pre-cooled and forced out of season for very uniform cut flower production.

The primary distinguishing feature of 'Orania' is its numerous, large, orange flowers. The seed parent, an Oriental type hybrid does not produce orange-yellow flowers like 'Orania' and 'Orania' can be bred approximately 25 days more quickly than the seed parent. The pollen parent, an Aurelia type hybrid, produces flowers having a different color than 'Orania.' Furthermore, the pollen parent has a different inflorescence, smaller flowers, and calyx-like flowers.

Asexual reproduction of this new variety has been accomplished at a nursery in Breezand, The Netherlands, by scaling and tissue culture. The resulting plants have shown that the above-mentioned unique features are stable and reproduce true to type in each successive propagation.

BRIEF DESCRIPTION OF THE DRAWING

This new variety of lily plant is illustrated in the accompanying photographic drawing which shows the upper half portion of the flowering stem of a potted plant in the full face view of the flowers together with some foliage. The accompanying photograph showing 'Orania' was taken in a studio and illustrates the typical flower and foliage form, with color as true as reasonably possible in this type of color illustration.

DETAILED BOTANICAL DESCRIPTION

This detailed description of the invention is based on plants approximately 80–90 days old and produced in greenhouses in Breezand, The Netherlands. Bulbs were planted in (and the resulting plants cultivated in) trays with peatmoss. Plants were grown at a minimum temperature of about 15° C. without supplemental fertilization or supplemental lighting. Color references are provided according to The R.H.S. Colour Chart published by The Royal Horticultural Society of London, England, except where the context indicates a term having its ordinary dictionary meaning.

Origin: Resulting from a hybridization.

Parentage:

*Seed parent.*—Oriental type hybrid lily 93.50.108-6 (proprietary owned).

*Pollen parent.*—Aurelia type hybrid lily 87.319-1 (proprietary owned).

Commercial classification: Upright Oriental×Aurelium hybrid lily, cut flower type.

Classification: Division VIII, all hybrids not provided for in any previous Division according to the Horticultural Classification of Lilies by The Royal Horticultural Society.

Form: Single erect stem from each bulb bearing terminal cluster of flowers.

*Height.*—To about 120 cm. from the top of the soil to the top of the inflorescence.

Stem: Green in color (RHS 141B).

Growth: Vigorous, upright, and very strong. Plants grew about 110 cm over a span of about 80 to 90 days.

Foliage:

*Arrangement.*—Incremental and staggered around the stem.

*Quantity.*—Abundant, approximately 45–50 leaves per plant.

*Leaf size.*—Variable, lower leaves on the stem about 16 cm. long and about 4 cm. wide; upper leaves on the stem about 16.6 cm long and about 5.5 cm wide. Leaves on the pedicel strongly recurve.

*Leaf shape.*—Lanceolate.

*Leaf margin.*—Entire.

*Aspect.*—Glossy.

*Texture.*—Leathery.

*Color.*—Upperside of leaves: Green (RHS139A). Bottomside of leaves: Green (RHS 137D). Leaf venation: Yellow-green (RHS 145A).

Bulb:

*Type.*—Concentric.

*Size.*—About 5.5 to 6.0 cm in diameter and about 16 to 18 cm in circumference.

*Color.*—Yellow-white (RHS 158C) and greyed-purple (RHS 184D).

Bud:

*Size.*—To about 12 cm. long and to about 3.2 cm wide.

*Shape.*—Lanceolate, with the apex commonly having three obtuse tips.

*Color.*—At first opening, the color is Orange (RHS 29D) blushed with Red Purple (RHS 63C) on the light side and Red (RHS 49D) on the shadow side changing to an Orange (RHS 25C) when unfurling.

*Opening rate.*—The mature bud opens slowly in response to light.

Flower:

*Blooming habit.*—Annually, once and profusely.

*Days to bloom.*—Flowers approximately 80 to 90 days after greenhouse planting under typical flower forcing conditions at minimum temperature of 15° C.

*Outdoor blooming time.*—Bulbs planted in mid-March bloom about mid-July.

*Greenhouse blooming time.*—Bulbs can be planted year-round and forced to bloom approximately 80 to 90 days after planting. Greenhouse bloom lasts about 12 to 15 days.

*Flower number.*—About 5 to 7 flowers per plant.

*Flower size.*—Large. Diameter: To about 21 cm. Depth: To about 8 cm.

*Borne.*—Umbel of about 3 to 5 flowers from bulbs of about 14 to 16 cm. in circumference.

*Shape.*—The flower is funnel shaped. After opening, the flower flattens and reflexes slightly, while the inner and the outer tepals recurve backwards at the tips.

*Tepalage.*—Number: 6. Arrangement: Imbricated. Shape: Oval. Texture: Leathery. Aspect: Glossy. Size: Length: Inner tepals to about 12 cm. Outer tepals to about 14.5 cm. Width: Inner tepals to about 6.6 cm. Outer tepals to about 4 cm. Nectary: Green (RHS 141A) from base to about 4.5 cm along midrib. Spots: None. Blush: None. Color: Outer tepals: Upper surface is yellow-orange (RHS 18B at the apex and around the edges, blending to RHS 20A in the middle with RHS 21A at the midline). Lower surface is yellow-orange (RHS 19C at apex and around the edges, blending to RHS 18C in the middle) with a red (RHS 48D) midline. Inner tepals: Upper surface is yellow-orange (RHS 18B at the apex and around the edges, blending to RHS 20A in the middle with RHS 21A at the midline). Lower surface is yellow-orange (RHS 19C) around the edges and red (RHS 48C) in the middle. Flower venation: Red (RHS 48D).

*Fragrance.*—Weak. Lasting Quality: Excellent. Each flower lasts about 14 days on the plant, with a vase life of about 12 to 15 days, depending upon environmental variables. Orientation: Ascending upwardly off the stem, the first flower at about a 40° angle, the last flower to about 80° degrees.

*Pedicel.*—Length: To about 11.5 cm. Color: Green (RHS 147A).

Reproductive organs:

*Stamens.*—Number: Six, typical of the genus Lilium.

*Anthers.*—Length: To about 2.3 cm. from mature bud. Color: Purple (RHS 185A).

*Filaments.*—Length: To about 9 cm. Color: Green (RHS 145C).

*Pollen.*—Color: Red (RHS 42B).

*Pistil.*—Number: One.

*Style.*—Length: About 7 cm. Color: Green (RHS 143C).

*Stigma.*—Color: Purple (RHS 59A).

Fruit:

*Fertility.*—Fruit is produced.

*Shape.*—Ovoid.

*Color at maturity.*—Green (RHS 145B).

Insect resistance: Some resistance to insects due to tough, leathery leaf.

Fungal resistance: Some resistance to Botrytis and Pytium species.

I claim:

1. A new and distinctive variety of oriental×Aurelia hybrid lily plant, substantially as herein illustrated and described.

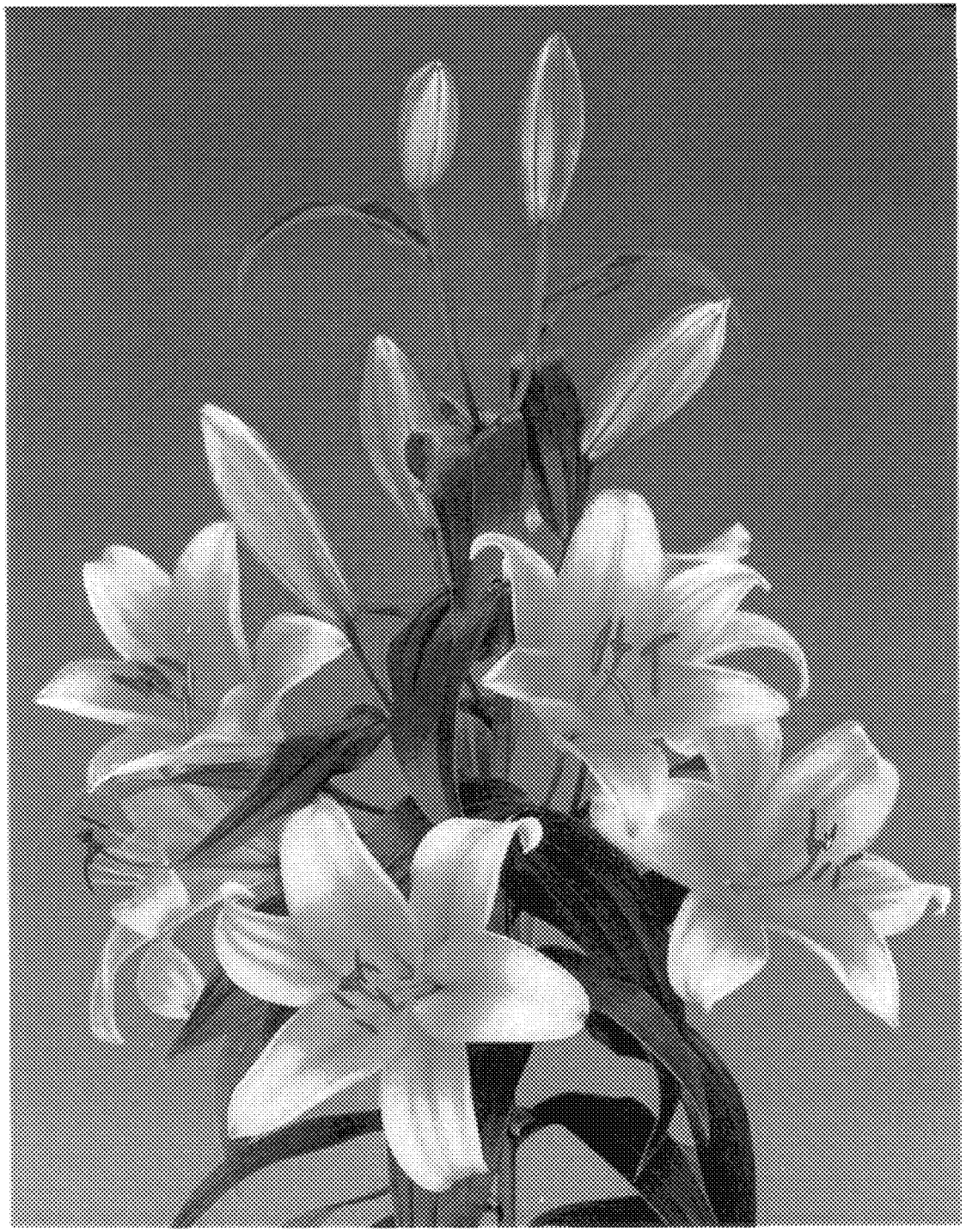

* * * * *